United States Patent
Dodson-Swenson

(10) Patent No.: US 11,277,985 B2
(45) Date of Patent: Mar. 22, 2022

(54) LETTUCE VARIETY BUCKSKIN

(71) Applicant: Syngenta Crop Protection AG, Basel (CH)

(72) Inventor: Hallie Gale Dodson-Swenson, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 13 days.

(21) Appl. No.: 16/779,826

(22) Filed: Feb. 3, 2020

(65) Prior Publication Data

US 2021/0235645 A1    Aug. 5, 2021

(51) Int. Cl.
*A01H 5/10* (2018.01)
*A01H 6/14* (2018.01)

(52) U.S. Cl.
CPC ............. *A01H 6/1472* (2018.05); *A01H 5/10* (2013.01)

(58) Field of Classification Search
CPC ................................. A01H 6/1472; A01H 5/12
See application file for complete search history.

(56) References Cited

U.S. PATENT DOCUMENTS 9,277,726 B2    3/2016   Holland
10,470,396 B2 *  11/2019  Heintzberger ........... A01H 5/12

OTHER PUBLICATIONS

PVP Certificate 200700155 dated Jun. 5, 2008.

* cited by examiner

*Primary Examiner* — Weihua Fan
(74) *Attorney, Agent, or Firm* — Karen A. Magri

(57) ABSTRACT

The present invention provides novel lettuce cultivar Buckskin and plant parts, seed, and tissue culture therefrom. The invention also provides methods for producing a lettuce plant by crossing the lettuce plants of the invention with themselves or another lettuce plant. The invention also provides lettuce plants produced from such a crossing as well as plant parts, seed, and tissue culture therefrom.

29 Claims, No Drawings

LETTUCE VARIETY BUCKSKIN

FIELD OF THE INVENTION

This invention is in the field of lettuce plants.

BACKGROUND OF THE INVENTION

The present invention relates to a lettuce (*Lactuca sativa* L.) variety designated Buckskin.

Practically speaking, all cultivated forms of lettuce belong to the highly polymorphic species *Lactuca sativa* that is grown for its edible head and leaves. *Lactuca sativa* is in the Cichoreae tribe of the Asteraceae (Compositae) family. Lettuce is related to chicory, sunflower, aster, dandelion, artichoke, and *chrysanthemum. Sativa* is one of about 300 species in the genus *Lactuca*. There are seven different morphological types of lettuce. The crisphead group includes the iceberg and batavian types. Iceberg lettuce has a large, firm head with a crisp texture and a white or creamy yellow interior. The batavian lettuce predates the iceberg type and has a smaller and less firm head. The butterhead group has a small, soft head with an almost oily texture. The romaine, also known as cos lettuce, has elongated upright leaves forming a loose, loaf-shaped head and the outer leaves are usually dark green. Leaf lettuce comes in many varieties, none of which form a head, and include the green oak leaf variety. Latin lettuce looks like a cross between romaine and butterhead. Stem lettuce has long, narrow leaves and thick, edible stems. Oilseed lettuce is a type grown for its large seeds that are pressed to obtain oil. Latin lettuce, stem lettuce, and oilseed lettuce are seldom seen in the United States.

Presently, there are over one thousand known lettuce cultivars. As a crop, lettuce is grown commercially wherever environmental conditions permit the production of an economically viable yield.

Lettuce, in general, and leaf lettuce in particular, is an important and valuable vegetable crop. Thus, there is an ongoing need for improved lettuce varieties.

SUMMARY OF THE INVENTION

According to the invention, there is provided a novel lettuce cultivar designated Buckskin, also known as LS15585. The invention also encompasses the seeds of lettuce cultivar Buckskin, the plants of lettuce cultivar Buckskin, plant parts of the lettuce cultivar Buckskin (including leaves, seed, gametes), methods of producing seed from lettuce cultivar Buckskin, and method for producing a lettuce plant by crossing the lettuce cultivar Buckskin with itself or another lettuce plant, methods for producing a lettuce plant containing in its genetic material one or more transgenes, and the transgenic lettuce plants produced by that method. The invention also relates to methods for producing other lettuce plants derived from lettuce cultivar Buckskin and to lettuce plants, parts thereof and seed derived by the use of those methods. The present invention further relates to hybrid lettuce seeds and plants (and parts thereof including leaves) produced by crossing lettuce cultivar Buckskin with another lettuce plant.

In another aspect, the present invention provides regenerable cells for use in tissue culture of lettuce cultivar Buckskin. In embodiments, the tissue culture is capable of regenerating plants having all or essentially all of the physiological and morphological characteristics of the foregoing lettuce plant and/or of regenerating plants having the same or substantially the same genotype as the foregoing lettuce plant. In exemplary embodiments, the regenerable cells in such tissue cultures are meristematic cells, cotyledons, hypocotyl, leaves, pollen, embryos, roots, root tips, anthers, pistils, ovules, shoots, stems, petiole, pith, flowers, capsules and/or seeds as well as callus and/or protoplasts derived from any of the foregoing. Still further, the present invention provides lettuce plants regenerated from the tissue cultures of the invention.

As a further aspect, the invention provides a method of producing lettuce seed, the method comprising crossing a plant of lettuce cultivar Buckskin with itself or a second lettuce plant. Optionally, the method further comprises collecting the seed.

Another aspect of the invention provides methods for producing hybrids and other lettuce plants derived from lettuce cultivar Buckskin. Lettuce plants derived by the use of those methods are also part of the invention as well as plant parts, seed, gametes and tissue culture from such hybrid or derived lettuce plants.

In representative embodiments, a lettuce plant derived from lettuce cultivar Buckskin comprises cells comprising at least one set of chromosomes derived from lettuce cultivar Buckskin. In embodiments, a lettuce plant or population of lettuce plants derived from lettuce cultivar Buckskin comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from lettuce cultivar Buckskin, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of lettuce cultivar Buckskin, and optionally is the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology. In embodiments, the lettuce plant derived from lettuce cultivar Buckskin is one, two, three, four, five or more breeding crosses removed from lettuce cultivar Buckskin.

In embodiments, a hybrid or derived plant from lettuce cultivar Buckskin comprises a desired added trait(s). In representative embodiments, a lettuce plant derived from lettuce cultivar Buckskin comprises all of the morphological and physiological characteristics of lettuce cultivar Buckskin (e.g., as described in Tables 1 to 14. In embodiments, the lettuce plant derived from lettuce cultivar Buckskin comprises essentially all of the morphological and physiological characteristics of lettuce cultivar Buckskin (e.g., as described in Tables 1 to 14, with the addition of a desired added trait(s).

The invention also relates to methods for producing a lettuce plant comprising in its genetic material one or more transgenes and to the transgenic lettuce plant produced by those methods (and progeny lettuce plants comprising the transgene). Also provided are plant parts, seed and tissue culture from such transgenic lettuce plants, optionally wherein one or more cells in the plant part, seed, or tissue culture comprises the transgene. The transgene can be introduced via plant transformation and/or breeding techniques.

In another aspect, the present invention provides for single gene converted plants of lettuce cultivar Buckskin. Plant parts, seed, and tissue culture from such single gene converted plants are also contemplated by the present invention. The single transferred gene may be a dominant or recessive allele. In representative embodiments, the single transferred gene confers such traits as male sterility, herbicide resistance, pest resistance (e.g., insect and/or nematode resistance), modified fatty acid metabolism, modified carbohydrate metabolism, disease resistance (e.g., for bacterial, fungal and/or viral disease), male fertility, enhanced nutritional quality, improved appearance (e.g., color), improved salt tolerance, industrial usage, or any combination thereof. The single gene may be a naturally occurring lettuce gene or a transgene introduced into lettuce through genetic engineering techniques.

The invention further provides methods for developing lettuce plants in a lettuce plant breeding program using plant breeding techniques including, for example, recurrent selection, backcrossing, pedigree breeding, double haploid techniques, restriction fragment length polymorphism enhanced selection, genetic marker enhanced selection and/or transformation. Seeds, lettuce plants, and parts thereof, produced by such breeding methods are also part of the invention.

The invention also provides methods of multiplication or propagation of lettuce plants of the invention, which can be accomplished using any method known in the art, for example, via vegetative propagation and/or seed.

The invention further provides a method of producing food or feed comprising (a) obtaining a lettuce plant of the invention, optionally wherein the plant has been cultivated to maturity, and (b) collecting at least one lettuce plant or part thereof (e.g., leaves) from the plant.

Additional aspects of the invention include harvested products and processed products from the lettuce plants of the invention. A harvested product can be a whole plant or any plant part, as described herein. Thus, in some embodiments, a non-limiting example of a harvested product includes a seed, a leaf and/or a stem.

In representative embodiments, a processed product includes, but is not limited to: cut, sliced, ground, pureed, dried, canned, jarred, washed, packaged, frozen and/or heated leaves and/or seeds of the lettuce plants of the invention, or any other part thereof. In embodiments, a processed product includes a sugar or other carbohydrate, fiber, protein and/or aromatic compound that is extracted, purified or isolated from a lettuce plant of the invention. In embodiments, the processed product includes washed and packaged leaves (or parts thereof) of the invention.

The seed of the invention can optionally be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

In representative embodiments, the invention provides a seed of lettuce cultivar Buckskin.

As a further aspect, the invention provides a plant of lettuce cultivar Buckskin.

As an additional aspect, the invention provides a lettuce plant, or a part thereof, having all or essentially all of the physiological and morphological characteristics of a plant of lettuce cultivar Buckskin.

As another aspect, the invention provides leaves and/or seed of the lettuce plants of the invention and a processed product from the leaves and/or seed of the inventive lettuce plants.

As still another aspect, the invention provides a method of producing lettuce seed, the method comprising crossing a lettuce plant of the invention with itself or a second lettuce plant. The invention also provides seed produced by this method and plants produced by growing the seed.

As yet a further aspect, the invention provides a method for producing a seed of a lettuce plant derived from lettuce cultivar Buckskin, the method comprising: (a) crossing a lettuce plant of lettuce cultivar Buckskin with a second lettuce plant; and (b) allowing seed of a lettuce plant derived from lettuce cultivar Buckskin to form. In embodiments, the method further comprises: (c) growing a plant from the seed derived from lettuce cultivar Buckskin of step (b); (d) selfing the plant grown from the lettuce seed derived from lettuce cultivar Buckskin or crossing it to a second lettuce plant to form additional lettuce seed derived from lettuce cultivar Buckskin, and (e) repeating steps (c) and (d) 0 or more times to generate further derived lettuce seed. Optionally, the method comprises: (e) repeating steps (c) and (d) one or more times (e.g., one to three, one to five, one to six, one to seven, one to ten, three to five, three to six, three to seven, three to eight or three to ten times) to generate further derived lettuce plants. As another option, the method can comprise collecting the seed. The invention also provides seed produced by these methods and plants produced by growing the seed.

As another aspect, the invention provides a method of producing lettuce leaves, the method comprising: (a) obtaining a plant of lettuce cultivar Buckskin, optionally wherein the plant has been cultivated to maturity; and (b) collecting leaves from the plant. The invention also provides the leaves produced by this method.

Still further, as another aspect, the invention provides a method of vegetatively propagating a plant of lettuce cultivar Buckskin. In a non-limiting example, the method comprises: (a) collecting tissue capable of being propagated from a plant of lettuce cultivar Buckskin; (b) cultivating the tissue to obtain proliferated shoots; and (c) rooting the proliferated shoots to obtain rooted plantlets. Optionally, the invention further comprises growing plants from the rooted plantlets. The invention also encompasses the plantlets and plants produced by these methods.

As an additional aspect, the invention provides a method of introducing a desired added trait into lettuce cultivar Buckskin, the method comprising: (a) crossing a first plant of lettuce cultivar Buckskin with a second lettuce plant that comprises a desired trait to produce $F_1$ progeny; (b) selecting an $F_1$ progeny that comprises the desired trait; (c) crossing the selected $F_1$ progeny with lettuce cultivar Buckskin to produce backcross progeny; and (d) selecting backcross progeny comprising the desired trait to produce a plant derived from lettuce cultivar Buckskin comprising a desired trait. In embodiments, the selected progeny comprises all or essentially all the morphological and physiological characteristics of the first plant of lettuce cultivar Buckskin. Optionally, the method further comprises: (e) repeating steps (c) and (d) one or more times in succession (e.g., one to three, one to five, one to six, one to seven, one to ten, three to five, three to six, three to seven, three to eight or three to ten times) to produce a plant derived from lettuce cultivar Buckskin comprising the desired trait.

In representative embodiments, the invention also provides a method of producing a plant of lettuce cultivar Buckskin comprising a desired added trait, the method comprising introducing a transgene conferring the desired trait into a plant of lettuce cultivar Buckskin. The transgene can be introduced by transformation methods (e.g., genetic engineering) or breeding techniques. In embodiments, the plant comprising the transgene comprises all or essentially all of the morphological and physiological characteristics of lettuce cultivar Buckskin.

The invention also provides lettuce plants produced by the methods of the invention, wherein the lettuce plant has the desired added trait as well as seed from such lettuce plants.

According to the foregoing methods, the desired added trait can be any suitable trait known in the art including, for example, male sterility, male fertility, herbicide resistance, insect or pest (e.g., insect and/or nematode) resistance, modified fatty acid metabolism, modified carbohydrate metabolism, disease resistance (e.g., for bacterial, fungal and/or viral disease), enhanced nutritional quality, increased sweetness, increased flavor, improved ripening control, improved salt tolerance, industrial usage, or any combination thereof.

In representative embodiments, a transgene conferring herbicide resistance confers resistance to glyphosate, sulfonylurea, imidazolinone, dicamba, glufosinate, phenoxy proprionic acid, L-phosphinothricin, cyclohexone, cyclohexanedione, triazine, benzonitrile, or any combination thereof.

In representative embodiments, a transgene conferring pest resistance (e.g., insect and/or nematode resistance) encodes a *Bacillus thuringiensis* endotoxin.

In representative embodiments, transgenic plants, transformed plants, hybrid plants and lettuce plants derived from lettuce cultivar Buckskin have at least 1, 2, 3, 4, 5, 6, 7, 8, 9, 10 or more of the morphological and physiological characteristics of lettuce cultivar Buckskin (e.g., as described in Tables 1 to 14) in any combination, or even all of the morphological and physiological characteristics of lettuce cultivar Buckskin, so that said plants are not significantly different for said traits than lettuce cultivar Buckskin, as determined at the 5% significance level when grown in the same environmental conditions; optionally, with the presence of one or more desired additional traits (e.g., male sterility, disease resistance, pest or insect resistance, herbicide resistance, and the like).

In embodiments, the plants of the invention have at least 1, 2, 3, 4, 5, 6, 7, 8, 9, 10 or more of the morphological and physiological characteristics of lettuce cultivar Buckskin (e.g., as described in Tables 1 to 14).

The invention also encompasses plant parts, plant material, pollen, ovules, leaves, fruit and seed from the lettuce plants of the invention. Also provided is a tissue culture of regenerable cells from the lettuce plants of the invention, where optionally, the regenerable cells are: (a) embryos, meristem, leaves, pollen, cotyledons, hypocotyls, roots, root tips, anthers, flowers, pistils, ovules, seed, shoots, stems, stalks, petioles, pith and/or capsules; or (b) callus or protoplasts derived from the cells of (a). Further provided are lettuce plants regenerated from a tissue culture of the invention.

In still yet another aspect, the invention provides a method of determining a genetic characteristic of lettuce cultivar Buckskin or a progeny thereof, e.g., a method of determining a genotype of lettuce cultivar Buckskin or a progeny thereof using molecular genetic techniques. In embodiments, the method comprises detecting in the genome of a Buckskin plant, or a progeny plant thereof, at least a first polymorphism, e.g., comprises nucleic acid amplification and/or nucleic acid sequencing. To illustrate, in embodiments, the method comprises obtaining a sample of nucleic acids from the plant and detecting at least a first polymorphism in the nucleic acid sample (e.g., using one or more molecular markers). Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

In addition to the exemplary aspects and embodiments described above, the invention is described in more detail in the description of the invention set forth below.

DETAILED DESCRIPTION OF THE INVENTION

The present invention is based, in part, on the development of a novel lettuce cultivar having desirable characteristics.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features and embodiments of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Definitions

In the description and tables that follow, a number of terms are used. In order to provide a clear and consistent understanding of the specification and claims, including the scope to be given such terms, the following definitions are provided:

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim or the description of this invention is not intended to be interpreted to be equivalent to "comprising."

"Allele". An allele is any of one or more alternative forms of a gene, all of which relate to a trait or characteristic. In a diploid cell or organism, the two alleles of a given gene occupy corresponding loci on a pair of homologous chromosomes.

"Backcrossing". Backcrossing is a process in which a breeder repeatedly crosses hybrid progeny back to one of the parents, for example, a first generation hybrid $F_1$ with one of the parental genotypes of the $F_1$ hybrid.

"Big Vein virus". Big vein is a disease of lettuce caused by Lettuce Mirafiori Big Vein Virus which is transmitted by the fungus *Olpidium virulentus*, with vein clearing and leaf shrinkage resulting in plants of poor quality and reduced marketable value.

"Bolting". The premature development of a flowering stalk, and subsequent seed, before a plant produces a food crop. Bolting is typically caused by late planting when temperatures are low enough to cause vernalization of the plants.

"*Bremia lactucae*". An Oomycete that causes downy mildew in lettuce in cooler growing regions.

"Core length". Length of the internal lettuce stem measured from the base of the cut and trimmed head to the tip of the stem.

"Corky root". A disease caused by the bacterium *Sphingomonas suberifaciens*, which causes the entire taproot to become brown, severely cracked, and non-functional.

"Cotyledon". One of the first leaves of the embryo of a seed plant; typically one or more in monocotyledons, two in dicotyledons, and two or more in gymnosperms.

"Double haploid line". A stable inbred line achieved by doubling the chromosomes of a haploid line, e.g., from anther culture. For example, some pollen grains (haploid) cultivated under specific conditions develop plantlets containing 1 n chromosomes. The chromosomes in these plantlets are then induced to "double" (e.g., using chemical means) resulting in cells containing 2n chromosomes. The progeny of these plantlets are termed "double haploid" and are essentially not segregating any more (e.g., are stable). The term "double haploid" is used interchangeably herein with "dihaploid."

"Essentially all of the physiological and morphological characteristics". In embodiments, a plant having "essentially all of the physiological and morphological characteristics" (and similar phrases) means a plant having the physiological and morphological characteristics of a parent plant (e.g., a recurrent parent), except for the characteristics derived from a converted gene(s) (i.e., via backcrossing to a recurrent parent), a modified gene(s) resulting from gene editing techniques, or an introduced transgene (i.e., introduced via genetic transformation techniques). In embodiments, a plant having "essentially all of the physiological and morphological characteristics" (and similar phrases) means a plant having all of the characteristics of the reference plant with the exception of five or fewer traits, 4 or fewer traits, 3 or fewer traits, 2 or fewer traits, or one trait.

"First water date". The date the seed first receives adequate moisture to germinate. This can and often does equal the planting date.

"Gene". As used herein, "gene" refers to a segment of nucleic acid comprising an open reading frame. A gene can be introduced into a genome of a species, whether from a different species or from the same species, using transformation or various breeding methods.

"Head diameter". Diameter of the cut and trimmed head, sliced vertically, and measured at the widest point perpendicular to the stem.

"Head height". Height of the cut and trimmed head, sliced vertically, and measured from the base of the cut stem to the cap leaf.

"Head weight". Weight of saleable lettuce head, cut and trimmed to market specifications.

"Inbred line": As used herein, the phrase "inbred line" refers to a genetically homozygous or nearly homozygous population. An inbred line, for example, can be derived through several cycles of sib crossing and/or selfing and/or via double haploid production. In some embodiments, inbred lines breed true for one or more traits of interest. An "inbred plant" or "inbred progeny" is an individual sampled from an inbred line.

"Lettuce Mosaic virus". A disease that can cause a stunted, deformed, or mottled pattern in young lettuce and yellow, twisted, and deformed leaves in older lettuce.

"Maturity date". Maturity refers to the stage when the plants are of full size and/or optimum weight and/or in marketable form to be of commercial or economic value.

"*Nasonovia ribisnigri*". A lettuce aphid that colonizes the innermost leaves of the lettuce plant, contaminating areas that cannot be treated easily with insecticides.

"Plant." As used herein, the term "plant" includes plant cells, plant protoplasts, plant cell tissue cultures from which plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, fruit, stems, and the like.

"Plant material". The terms "plant material" and "material obtainable from a plant" are used interchangeably herein and refer to any plant material obtainable from a plant including without limitation, leaves, stems, roots, flowers or flower parts, fruits, pollen, ovules, zygotes, seeds, cuttings, cell or tissue cultures, or any other part or product of the plant.

"Plant part". As used herein, a "plant part" includes any part, organ, tissue or cell of a plant including without limitation an embryo, meristem, leaf, pollen, cotyledon, hypocotyl, root, root tip, anther, flower, flower bud, pistil, ovule, seed, shoot, stem, stalk, petiole, pith, capsule, a scion, a rootstock and/or a fruit including callus and protoplasts derived from any of the foregoing.

"Quantitative Trait Loci". Quantitative Trait Loci (QTL) refers to genetic loci that control to some degree, numerically representable traits that are usually continuously distributed.

"Ratio of head height/diameter". Head height divided by the head diameter is an indication of the head shape; <1 is flattened, 1=round, and >1 is pointed.

"Regeneration". Regeneration refers to the development of a plant from tissue culture.

"Resistance". As used herein the terms "resistance" and "tolerance" (and grammatical variations thereof) are used interchangeably to describe plants that show reduced or essentially no symptoms to a specific biotic (e.g., a pest, pathogen or disease) or abiotic (e.g., exogenous or environmental, including herbicides) factor or stressor. In some embodiments, "resistant" or "tolerant" plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. A lettuce plant may be considered "resistant" or "tolerant" if resistance/tolerance is observed over a plurality of plants (e.g., an average), even if particular individual plants may be susceptible to the biotic or abiotic factor or stressor.

"RHS". RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

"Single gene converted". A single gene converted or conversion plant refers to a plant that is developed by plant breeding techniques (e.g., backcrossing) or via genetic engineering wherein essentially all of the desired morphological and physiological characteristics of a line are recovered in addition to the single gene transferred into the line via the plant breeding technique or via genetic engineering.

"Substantially equivalent characteristic". A characteristic that, when compared, does not show a statistically significant difference (e.g., $p=0.05$) from the mean.

"Tip burn". Means a browning of the edges or tips of lettuce leaves that is a physiological response to a lack of calcium.

"Tomato Bushy Stunt". Also called "lettuce necrotic stunt". A disease that causes stunting of growth and leaf mottling.

"Transgene". A nucleic acid of interest that can be introduced into the genome of a plant by genetic engineering techniques (e.g., transformation) or breeding. The transgene can be from the same or a different species. If from the same species, the transgene can be an additional copy of a native coding sequence or can present the native sequence in a form or context (e.g., different genomic location and/or in operable association with exogenous regulatory elements such as a promoter) than is found in the native state. The transgene can comprise an open reading frame encoding a polypeptide or can encode a functional non-translated RNA (e.g., RNAi).

Botanical Description of the Lettuce Cultivar Buckskin (LS15585).

Characteristics. Lettuce cultivar Buckskin is an iceberg lettuce variety. Lettuce variety Buckskin resulted from a cross between lettuce lines, subsequent backcrosses and several generations of individual plant selections chosen for downy mildew resistance, head shape, and head size.

Lettuce Buckskin has shown uniformity and stability for all traits, within the limits of environmental influence. It has been self-pollinated a sufficient number of generations with careful attention to uniformity of plant type. The variety has been increased with continued observation for uniformity. No variant traits have been observed or are expected in lettuce cultivar Buckskin.

TABLE 1

Variety Description Information.

Plant Type: Iceberg
Seed
Seed color: Black
Light dormancy: Light not required
Heat dormancy: Susceptible
Cotyledon to Fourth Leaf Stage Shape of cotyledons: Broad
Shape of $4^{th}$ leaf: Elongated
Apical margin: Crenate
Basel margin: Moderately dentate
Undulation: Medium
Anthocyanin distribution: Absent
Rolling: Absent
Cupping: Uncupped
Reflexing: Apical and Lateral Margin
Mature Leaves Margin incision depth: Absent/shallow
Margin indentation: Shallow dentate
Margin undulation of the apical margin: Absent/slight
Green color: Medium green
Anthocyanin distribution: Absent
Glossiness: Moderate
Blistering: Absent/slight
Trichomes: Absent
Leaf thickness: Intermediate
Plant at Market Stage Head shape: Spherical
Head size class: Large
Head weight (g): 909
Head firmness: Moderate
Butt shape: Rounded
Butt midrib: Prominently raised

TABLE 1-continued

Variety Description Information.

Core

Diameter at base of head (mm): 34.85
Core height from base of head to apex (mm): 46.85
Maturity (days)

Winter: 105 to 110 days
Adaptation

Primary U.S. Regions of Adaptation (tested and proven adapted)
Southwest (California, Arizona desert): Yes
West Coast: Not adapted
Southeast: Not tested
Northeast: Not tested
Spring area: Not adapted
Summer area: Not adapted
Fall area: Not adapted
Winter area: Yuma (Arizona), Imperial (California)
Greenhouse: Not tested
Soil type: Both of mineral and organic
Disease and Stress Reactions
Virus Tomato Bushy Stunt virus (TBSV): Highly resistant
Big vein: Not tested
Cucumber Mosaic virus: Not tested
Broad Bean Wilt: Not tested
Turnip Mosaic virus: Not tested
Best Western Yellows: Not tested
Lettuce Infectious Yellows: Not tested
Lettuce Mosaic virus (LMV) strain Ls-1: Susceptible
Fungal/Bacterial Corky Root Rot (Pythium Root Rot): Not tested
Bremia lactucae (Downy Mildew): Highly resistant to Bl: 16-26, 28, 32EU and 5-9US
Powdery Mildew: Not tested
Sclerotinia Rot: Not tested
Bacterial Soft Rot (*Pseudomonas* spp. & others): Not tested
Botrytis (Gray Mold): Not tested
Insects Nasonovia biotype Nr: 0: Susceptible
Cabbage Loopers: Not tested
Root Aphids: Not tested
Green Peach Aphid: Not tested
Physiological/Stress Tip burn: Not tested
Heat: Not tested
Drought: Not tested
Cold: Intermediate
Salt: Not tested
Brown Rib: Not tested
Post-Harvest Pink Rib: Not tested
Russett Spotting: Not tested
Rusty Brown Discoloration: Not tested
Internal Rib Necrosis (Blackheart, Gray Rib, Gray Streak): Not tested
Brown Stain: Not tested

TABLE 2

Length (mm) of 4th Leaf at 20 Days

| Buckskin | Quest | Pennylea |
|---|---|---|
| 30 | 33 | 20 |
| 30 | 22 | 25 |
| 35 | 18 | 22 |
| 30 | 23 | 16 |
| 32 | 18 | 22 |
| 30 | 25 | 28 |
| 30 | 23 | 24 |
| 32 | 18 | 23 |
| 30 | 26 | 15 |
| 30 | 22 | 34 |
| 33 | 20 | 22 |
| 28 | 20 | 25 |
| 32 | 20 | 21 |
| 33 | 25 | 18 |
| 40 | 19 | 32 |
| 33 | 33 | 22 |
| 32 | 23 | 22 |
| 28 | 23 | 14 |

TABLE 2-continued

Length (mm) of 4th Leaf at 20 Days

| 27 | 30 | 22 |
|---|---|---|
| 29 | 32 | 28 |

| ANOVA Source of Variation | Response Variable: | Length (mm) of 4th Leaf at 20 Days | | |
|---|---|---|---|---|
| | df | SS | MS | F | P-value |
| Variety | 2 | 861.43 | 11.03 | 430.72 | <0.0001 |

| Variety | Mean | Tukey HSD Grouping |
|---|---|---|
| Buckskin | 31.20 | a |
| Quest | 23.65 | b |
| Pennylea | 22.75 | b |

ANOVA shows a significant difference (p < 0.05) in the length (mm) of 4th leaf at 20 days, and the average length (mm) of 4th leaf for Buckskin, Quest, and Pennylea is 31.20, 23.65, and 22.75, respectively. However, based on the Tukey HSD grouping, there are no differences between means for Quest and Pennylea.

TABLE 3

Width (mm) of 4th Leaf at 20 Days

| Buckskin | Quest | Pennylea |
|---|---|---|
| 15 | 25 | 13 |
| 15 | 20 | 18 |
| 18 | 15 | 18 |
| 13 | 16 | 10 |
| 20 | 12 | 15 |
| 22 | 20 | 11 |
| 17 | 12 | 15 |
| 18 | 12 | 17 |
| 12 | 20 | 10 |
| 15 | 17 | 20 |
| 16 | 10 | 12 |
| 14 | 15 | 13 |
| 17 | 12 | 18 |
| 20 | 19 | 12 |
| 23 | 9 | 19 |
| 19 | 20 | 13 |
| 18 | 15 | 12 |
| 14 | 17 | 10 |
| 15 | 20 | 12 |
| 17 | 19 | 16 |

| ANOVA Source of Variation | Response Variable: | Width (mm) of 4th Leaf at 20 Days | | | |
|---|---|---|---|---|---|
| | df | SS | MS | F | P-value |
| Variety | 2 | 79.43 | 39.77 | 3.27 | 0.0453 |

| Variety | Mean | Tukey HSD Grouping |
|---|---|---|
| Buckskin | 16.90 | a |
| Quest | 16.25 | ab |
| Pennylea | 14.20 | b |

ANOVA shows a significant difference (p < 0.05) in the width (mm) of 4th leaf at 20 days, and the average width (mm) of 4th leaf for Buckskin, Quest, and Pennylea is 16.90, 16.25, and 14.20, respectively. However, based on the Tukey HSD grouping, there are only differences between means for Buckskin and Pennylea.

TABLE 4

Length to Width index of 4th Leaf at 20 Days

| Buckskin | Quest | Pennylea |
|---|---|---|
| 2.00 | 1.32 | 1.54 |
| 2.00 | 1.10 | 1.39 |
| 1.94 | 1.20 | 1.22 |
| 2.31 | 1.44 | 1.60 |
| 1.60 | 1.50 | 1.47 |
| 1.36 | 1.25 | 2.55 |
| 1.76 | 1.92 | 1.60 |
| 1.78 | 1.50 | 1.35 |
| 2.50 | 1.30 | 1.50 |
| 2.00 | 1.29 | 1.70 |
| 2.06 | 2.00 | 1.83 |
| 2.00 | 1.33 | 1.92 |
| 1.88 | 1.67 | 1.17 |
| 1.65 | 1.32 | 1.50 |
| 1.74 | 2.11 | 1.68 |
| 1.74 | 1.65 | 1.69 |
| 1.78 | 1.53 | 1.83 |
| 2.00 | 1.35 | 1.40 |
| 1.80 | 1.50 | 1.83 |
| 1.71 | 1.68 | 1.75 |

| ANOVA Source of Variation | Response Variable: | Length to Width index of 4th Leaf at 20 Days | | | |
|---|---|---|---|---|---|
| | df | SS | MS | F | P-value |
| Variety | 2 | 1.52 | 0.76 | 10.09 | 0.0002 |

| Variety | Mean | Tukey HSD Grouping |
|---|---|---|
| Buckskin | 1.88 | a |
| Pennylea | 1.62 | b |
| Quest | 1.50 | b |

ANOVA shows a significant difference (p < 0.05) in the length to width index of 4th leaf at 20 Days, and the average length to width for Buckskin, Pennylea, and Quest is 1.88, 1.62, and 1.50, respectively. However, based on the Tukey HSD grouping, there are no differences between means for Pennylea and Quest.

TABLE 5

Length (mm) of Cotyledon at 20 Days

| Buckskin | Quest | Pennylea |
|---|---|---|
| 13 | 13 | 16 |
| 12 | 12 | 11 |
| 13 | 11 | 11 |
| 13 | 13 | 11 |
| 10 | 11 | 12 |
| 11 | 15 | 10 |
| 12 | 12 | 14 |
| 12 | 15 | 11 |
| 12 | 13 | 10 |
| 13 | 12 | 12 |
| 13 | 13 | 10 |
| 12 | 13 | 12 |
| 12 | 12 | 11 |
| 11 | 13 | 11 |
| 10 | 12 | 10 |
| 10 | 12 | 10 |
| 13 | 12 | 11 |
| 12 | 10 | 11 |
| 12 | 12 | 10 |
| 10 | 11 | 10 |

TABLE 5-continued

Length (mm) of Cotyledon at 20 Days

| ANOVA Source of Variation | Response Variable: | Length (mm) of Cotyledon at 20 Days | | | |
|---|---|---|---|---|---|
| | df | SS | MS | F | P-value |
| Variety | 2 | 13.23 | 6.62 | 3.97 | 0.0243 |

| Variety | Mean | Tukey HSD Grouping |
|---|---|---|
| Quest | 12.35 | a |
| Buckskin | 11.80 | ab |
| Pennylea | 11.20 | b |

ANOVA shows a significant difference ($p < 0.05$) in the length (mm) of cotyledon at 20 days, and the average length (mm) of cotyledon for Quest, Buckskin, and Pennylea is 12.35, 11.80, and 11.20, respectively. However, based on the Tukey HSD grouping, there are only differences between means for Quest and Pennylea.

TABLE 6

Width (mm) of Cotyledon Leaf at 20 Days

| Buckskin | Quest | Pennylea |
|---|---|---|
| 9 | 9 | 10 |
| 10 | 8 | 9 |
| 8 | 8 | 9 |
| 10 | 8 | 8 |
| 8 | 7 | 10 |
| 9 | 9 | 10 |
| 8 | 9 | 8 |
| 10 | 8 | 8 |
| 9 | 8 | 8 |
| 9 | 8 | 10 |
| 10 | 8 | 9 |
| 10 | 8 | 9 |
| 10 | 8 | 8 |
| 10 | 10 | 9 |
| 8 | 8 | 7 |
| 9 | 8 | 8 |
| 11 | 7 | 7 |
| 9 | 7 | 9 |
| 8 | 10 | 9 |
| 9 | 8 | 8 |

TABLE 6-continued

Width (mm) of Cotyledon Leaf at 20 Days

| ANOVA Source of Variation | Response variable: | Width (mm) of Cotyledon leaf at 20 Days | | | |
|---|---|---|---|---|---|
| | df | SS | MS | F | P-value |
| Variety | 2 | 10.03 | 5.02 | 6.36 | 0.0032 |

| Variety | Mean | Tukey HSD Grouping |
|---|---|---|
| Buckskin | 9.20 | a |
| Pennylea | 8.65 | ab |
| Quest | 8.20 | b |

ANOVA shows a significant difference ($p < 0.05$) in the width (mm) of cotyledon at 20 days, and the average width (mm) of cotyledon for Buckskin, Pennylea, and Quest is 9.20, 8.65, and 8.20, respectively. However, based on the Tukey HSD grouping, there are only differences between means for Buckskin and Quest.

TABLE 7

Length to Width index of Cotyledon Leaf at 20 Days

| Buckskin | Quest | Pennylea |
|---|---|---|
| 1.44 | 1.44 | 1.60 |
| 1.20 | 1.50 | 1.22 |
| 1.63 | 1.38 | 1.22 |
| 1.30 | 1.63 | 1.38 |
| 1.25 | 1.57 | 1.20 |
| 1.22 | 1.67 | 1.00 |
| 1.50 | 1.33 | 1.75 |
| 1.20 | 1.88 | 1.38 |
| 1.33 | 1.63 | 1.25 |
| 1.44 | 1.50 | 1.20 |
| 1.30 | 1.63 | 1.11 |
| 1.20 | 1.63 | 1.33 |
| 1.20 | 1.50 | 1.38 |
| 1.10 | 1.30 | 1.22 |
| 1.25 | 1.50 | 1.43 |
| 1.11 | 1.50 | 1.25 |
| 1.18 | 1.71 | 1.57 |
| 1.33 | 1.43 | 1.22 |
| 1.50 | 1.20 | 1.11 |
| 1.11 | 1.38 | 1.25 |

| ANOVA Source of Variation | Response Variable: | Length to width index of Cotyledon leaf at 20 Days | | | |
|---|---|---|---|---|---|
| | df | SS | MS | F | P-value |
| Variety | 2 | 0.64 | 0.32 | 12.15 | <0.0001 |

| Variety | Mean | Tukey HSD Grouping |
|---|---|---|
| Quest | 1.52 | a |
| Pennylea | 1.30 | b |
| Buckskin | 1.29 | b |

ANOVA shows a significant difference ($p < 0.05$) in the length to width index of cotyledon leaf at 20 days, and the average length to width index for Quest, Pennylea, and Buckskin is 1.52, 1.30, and 1.29, respectively. However, based on the Tukey HSD grouping, there are no differences between means for Pennylea and Buckskin.

TABLE 8

Head Weight (g) at Harvest Maturity

| Buckskin Loc. 1 | Quest Loc. 1 | Pennylea Loc. 1 | Buckskin Loc. 2 | Quest Loc. 2 | Pennylea Loc. 2 | Buckskin Loc. 3 | Quest Loc. 3 | Pennylea Loc. 3 |
|---|---|---|---|---|---|---|---|---|
| 639 | 791 | 856 | 1149 | 1083 | 992 | 883 | 507 | 475 |
| 1033 | 574 | 957 | 758 | 758 | 1387 | 735 | 1086 | 364 |
| 972 | 1010 | 721 | 1694 | 1132 | 655 | 754 | 994 | 605 |
| 651 | 773 | 959 | 863 | 1102 | 1020 | 912 | 880 | 440 |
| 946 | 499 | 641 | 770 | 639 | 827 | 892 | 725 | 639 |

TABLE 8-continued

Head Weight (g) at Harvest Maturity

| | | | | | | | | |
|---|---|---|---|---|---|---|---|---|
| 793 | 803 | 1004 | 689 | 724 | 997 | 851 | 668 | 715 |
| 844 | 642 | 698 | 1050 | 1033 | 784 | 925 | 876 | 639 |
| 1104 | 691 | 756 | 700 | 1099 | 1139 | 670 | 992 | 424 |
| 1095 | 950 | 880 | 1283 | 1174 | 1258 | 813 | 1263 | 715 |
| 968 | 719 | 784 | 794 | 1147 | 915 | 687 | 965 | 393 |
| 1006 | 765 | 1020 | | | | | | |
| 890 | 590 | 786 | | | | | | |
| 859 | 1049 | 549 | | | | | | |
| 910 | 949 | 734 | | | | | | |
| 938 | 826 | 895 | | | | | | |
| 1055 | 772 | 851 | | | | | | |
| 751 | 903 | 886 | | | | | | |
| 963 | 920 | 929 | | | | | | |
| 984 | 647 | 908 | | | | | | |
| 1096 | 959 | 829 | | | | | | |

| ANOVA | Response Variable: | Head Weight (g) at Harvest Maturity | | | | |
|---|---|---|---|---|---|---|
| Source of Variation | df | SS | MS | F | P-value | |
| Variety | 2 | 239635 | 232083 | 3.789 | 0.0256 | * |
| Location | 2 | 857447 | 428724 | 13.559 | <0.0001 | *** |
| Variety:Location | 4 | 637456 | 159364 | 5.040 | 0.0009 | *** |

| Variety | Mean | Duncan Grouping |
|---|---|---|
| Buckskin | 909 | a |
| Quest | 867 | ab |
| Pennylea | 801 | b |

ANOVA shows significant differences (p < 0.05) in head weight (g) at harvest maturity stage for variety, location, and in the interaction between variety and location. The average head weight (g) of Buckskin, Quest, and Pennylea are 909, 867, and 801, respectively.

TABLE 9

Length of Frame Leaves (cm) at Harvest Maturity

| Buckskin Loc. 1 | Quest Loc. 1 | Pennylea Loc. 1 | Buckskin Loc. 2 | Quest Loc. 2 | Pennylea Loc. 2 | Buckskin Loc. 3 | Quest Loc. 3 | Pennylea Loc. 3 |
|---|---|---|---|---|---|---|---|---|
| 29.00 | 23.00 | 28.00 | 23.00 | 24.00 | 23.00 | 28.10 | 27.40 | 25.10 |
| 31.00 | 23.00 | 24.00 | 24.00 | 24.00 | 26.00 | 27.10 | 28.20 | 27.00 |
| 23.00 | 25.00 | 21.00 | 24.00 | 27.00 | 23.00 | 28.00 | 27.10 | 24.40 |
| 23.00 | 26.00 | 24.00 | 23.00 | 20.00 | 24.00 | 27.60 | 29.00 | 29.10 |
| 23.00 | 24.00 | 24.00 | 24.00 | 25.00 | 30.00 | 26.40 | 30.50 | 26.80 |
| 26.00 | 26.00 | 22.00 | 23.00 | 22.00 | 25.00 | 27.40 | 26.80 | 27.10 |
| 24.00 | 29.00 | 24.00 | 25.00 | 24.00 | 23.00 | 24.00 | 28.70 | 27.40 |
| 27.00 | 25.00 | 25.00 | 23.00 | 22.00 | 25.00 | 28.90 | 32.20 | 22.90 |
| 28.00 | 29.00 | 25.00 | 24.00 | 23.00 | 23.00 | 24.90 | 24.20 | 26.30 |
| 29.00 | 30.00 | 24.00 | 19.00 | 18.00 | 21.00 | 26.00 | 31.10 | 25.90 |
| 27.00 | 26.00 | 23.00 | | | | | | |
| 25.00 | 21.00 | 24.00 | | | | | | |
| 22.00 | 28.00 | 28.00 | | | | | | |
| 27.00 | 26.00 | 27.00 | | | | | | |
| 24.00 | 26.00 | 25.00 | | | | | | |
| 27.00 | 28.00 | 25.00 | | | | | | |
| 24.00 | 27.00 | 26.00 | | | | | | |
| 26.00 | 25.00 | 25.00 | | | | | | |
| 21.00 | 30.00 | 25.00 | | | | | | |
| 24.00 | 21.00 | 25.00 | | | | | | |

TABLE 9-continued

Length of Frame Leaves (cm) at Harvest Maturity

| ANOVA | Response Variable: | Length of Frame Leaves (cm) at Harvest Maturity | | | | |
|---|---|---|---|---|---|---|
| Source of Variation | df | SS | MS | F | P-value | |
| Variety | 2 | 14.2 | 7.11 | 1.423 | 0.2453 | ** |
| Location | 2 | 207.6 | 103.81 | 20.765 | <0.0001 | * |
| Variety:Location | 4 | 40.3 | 10.07 | 2.015 | 0.0973 | |

| Variety | Mean | Duncan Grouping |
|---|---|---|
| Quest | 25.81 | a |
| Buckskin | 25.26 | a |
| Pennylea | 24.98 | a |

ANOVA shows no significant difference (p > 0.05) in length of frame leaves (cm) at harvest maturity between varieties and the interaction between variety by location, but it did show significant difference (p < 0.0001) between locations.

TABLE 10

Width of Frame Leaves (cm) at Harvest Maturity

| Buckskin Loc. 1 | Quest Loc. 1 | Pennylea Loc. 1 | Buckskin Loc. 2 | Quest Loc. 2 | Pennylea Loc. 2 | Buckskin Loc. 3 | Quest Loc. 3 | Pennylea Loc. 3 |
|---|---|---|---|---|---|---|---|---|
| 32.00 | 21.00 | 24.00 | 26.00 | 26.00 | 26.00 | 30.90 | 31.40 | 28.00 |
| 29.00 | 24.00 | 19.00 | 23.00 | 28.00 | 34.00 | 29.00 | 24.20 | 26.60 |
| 24.00 | 25.00 | 18.00 | 28.00 | 36.00 | 26.00 | 36.90 | 28.40 | 24.00 |
| 19.00 | 24.00 | 18.00 | 27.00 | 19.00 | 32.00 | 29.80 | 26.00 | 27.00 |
| 24.00 | 27.00 | 19.00 | 24.00 | 26.00 | 32.00 | 32.70 | 40.40 | 31.90 |
| 29.00 | 22.00 | 17.00 | 24.00 | 21.00 | 32.00 | 31.00 | 30.90 | 27.30 |
| 15.00 | 28.00 | 20.00 | 22.00 | 24.00 | 24.00 | 24.00 | 30.60 | 26.90 |
| 25.00 | 23.00 | 20.00 | 27.00 | 25.00 | 30.00 | 37.60 | 29.50 | 23.10 |
| 26.00 | 25.00 | 23.00 | 26.00 | 27.00 | 28.00 | 31.70 | 25.20 | 26.60 |
| 25.00 | 27.00 | 21.00 | 22.00 | 20.00 | 24.00 | 35.00 | 32.40 | 29.90 |
| 19.00 | 25.00 | 20.00 | | | | | | |
| 21.00 | 23.00 | 25.00 | | | | | | |
| 16.00 | 21.00 | 22.00 | | | | | | |
| 19.00 | 22.00 | 23.00 | | | | | | |
| 18.00 | 19.00 | 22.00 | | | | | | |
| 24.00 | 19.00 | 18.00 | | | | | | |
| 19.00 | 20.00 | 17.00 | | | | | | |
| 25.00 | 23.00 | 29.00 | | | | | | |
| 20.00 | 26.00 | 16.00 | | | | | | |
| 21.00 | 18.00 | 22.00 | | | | | | |

| ANOVA | Response Variable: | Width of Frame Leaves (cm) at Harvest Maturity | | | | |
|---|---|---|---|---|---|---|
| Source of Variation | df | SS | MS | F | P-value | |
| Variety | 2 | 31.1 | 15.5 | 1.140 | 0.3233 | ** |
| Location | 2 | 1204.2 | 602.1 | 44.183 | <0.0001 | * |
| Variety:Location | 4 | 241.3 | 60.3 | 4.427 | 0.0023 | ** |

| Variety | Mean | Duncan Grouping |
|---|---|---|
| Buckskin | 25.44 | a |
| Quest | 25.33 | a |
| Pennylea | 24.31 | a |

ANOVA shows no significant difference (p > 0.05) in width of frame leaves (cm) at harvest maturity between varieties, but it did show significant differences between locations (p < 0.0001) and the interaction between variety by location (p = 0.0023).

TABLE 11

Length to Width index of Frame Leaves (cm) at Harvest Maturity

| Buckskin Loc. 1 | Quest Loc. 1 | Pennylea Loc. 1 | Buckskin Loc. 2 | Quest Loc. 2 | Pennylea Loc. 2 | Buckskin Loc. 3 | Quest Loc. 3 | Pennylea Loc. 3 |
|---|---|---|---|---|---|---|---|---|
| 0.91 | 1.10 | 1.17 | 0.88 | 0.92 | 0.88 | 0.91 | 0.87 | 0.90 |
| 1.07 | 0.96 | 1.26 | 1.04 | 0.86 | 0.76 | 0.93 | 1.17 | 1.02 |

TABLE 11-continued

Length to Width index of Frame Leaves (cm) at Harvest Maturity

| | | | | | | | | |
|---|---|---|---|---|---|---|---|---|
| 0.96 | 1.00 | 1.17 | 0.86 | 0.75 | 0.88 | 0.76 | 0.95 | 1.02 |
| 1.21 | 1.08 | 1.33 | 0.85 | 1.05 | 0.75 | 0.93 | 1.12 | 1.08 |
| 0.96 | 0.89 | 1.26 | 1.00 | 0.96 | 0.94 | 0.81 | 0.75 | 0.84 |
| 0.90 | 1.18 | 1.29 | 0.96 | 1.05 | 0.78 | 0.88 | 0.87 | 0.99 |
| 1.60 | 1.04 | 1.20 | 1.14 | 1.00 | 0.96 | 1.00 | 0.94 | 1.02 |
| 1.08 | 1.09 | 1.25 | 0.85 | 0.88 | 0.83 | 0.77 | 1.09 | 0.99 |
| 1.08 | 1.16 | 1.09 | 0.92 | 0.85 | 0.82 | 0.79 | 0.96 | 0.99 |
| 1.16 | 1.11 | 1.14 | 0.86 | 0.90 | 0.88 | 0.74 | 0.96 | 0.87 |
| 1.42 | 1.04 | 1.15 | | | | | | |
| 1.19 | 0.91 | 0.96 | | | | | | |
| 1.38 | 1.33 | 1.27 | | | | | | |
| 1.42 | 1.18 | 1.17 | | | | | | |
| 1.33 | 1.37 | 1.14 | | | | | | |
| 1.13 | 1.47 | 1.39 | | | | | | |
| 1.26 | 1.35 | 1.53 | | | | | | |
| 1.04 | 1.09 | 0.86 | | | | | | |
| 1.05 | 1.15 | 1.56 | | | | | | |
| 1.14 | 1.17 | 1.14 | | | | | | |

| ANOVA Source of Variation | Response Variable: df | Length to Width index of Frame Leaves (cm) at Harvest Maturity SS | MS | F | P-value | |
|---|---|---|---|---|---|---|
| Variety | 2 | 0.0244 | 0.0122 | 0.640 | 0.5292 | ** |
| Location | 2 | 1.9656 | 0.9828 | 51.501 | <0.0001 | * |
| Variety:Location | 4 | 0.1836 | 0.0459 | 2.405 | 0.0539 | |

| Variety | Mean | Duncan Grouping |
|---|---|---|
| Pennylea | 1.06 | a |
| Quest | 1.04 | a |
| Buckskin | 1.03 | a |

ANOVA shows no significant difference (p > 0.05) in length to width index of frame leaves (cm) at harvest maturity between varieties and the interaction between variety by location, but it did show significant difference (p < 0.0001) between locations.

TABLE 12

Height (cm) of Mature Seed Stalk

| Buckskin | Quest | Pennylea |
|---|---|---|
| 154.94 | 139.70 | 106.68 |
| 152.40 | 144.78 | 114.30 |
| 157.48 | 142.24 | 109.22 |
| 165.10 | 139.70 | 104.14 |
| 167.64 | 142.24 | 104.14 |
| 170.18 | 142.24 | 109.22 |
| 147.32 | 137.16 | 111.76 |
| 154.94 | 134.62 | 104.14 |
| 154.94 | 139.70 | 101.60 |
| 154.94 | 132.08 | 101.60 |
| 154.94 | 139.70 | 101.60 |
| 154.94 | 139.70 | 116.84 |
| 152.40 | 139.70 | 119.38 |
| 157.48 | 137.16 | 114.30 |
| 160.02 | 134.62 | 106.68 |
| 154.94 | 132.08 | 104.14 |
| 154.94 | 142.24 | 101.60 |
| 157.48 | 139.70 | 106.68 |
| 157.48 | 137.16 | 106.68 |
| 154.94 | 134.62 | 109.22 |

| ANOVA Source of Variation | Response Variable: df | Height (cm) of Mature Seed Stalk SS | MS | F | P-value |
|---|---|---|---|---|---|
| Variety | 2 | 24797.59 | 12398.80 | 539.76 | <0.0001 |

| Variety | Mean | Tukey HSD Grouping |
|---|---|---|
| Buckskin | 156.97 | a |
| Quest | 138.56 | b |
| Pennylea | 107.70 | c |

ANOVA shows a significant difference (p < 0.05) in the height of mature seed stalk, and the average mature seed stalk height (cm) for Buckskin, Quest, and Pennylea is 156.97, 138.56, and 107.70, respectively.

TABLE 13

Spread (cm) of Mature Seed Stalk at Widest Point

| Buckskin | Quest | Pennylea |
|---|---|---|
| 63.50 | 45.72 | 68.58 |
| 60.96 | 45.72 | 66.04 |
| 58.42 | 43.18 | 66.04 |
| 58.42 | 40.64 | 63.50 |
| 55.88 | 40.64 | 53.34 |
| 63.50 | 45.72 | 66.04 |
| 66.04 | 45.72 | 58.42 |
| 68.58 | 48.26 | 63.50 |
| 63.50 | 45.72 | 60.96 |
| 63.50 | 50.80 | 53.34 |

TABLE 13-continued

Spread (cm) of Mature Seed Stalk at Widest Point

| 60.96 | 43.18 | 53.34 |
|---|---|---|
| 63.50 | 45.72 | 63.50 |
| 58.42 | 45.72 | 63.50 |
| 63.50 | 48.26 | 63.50 |
| 63.50 | 45.72 | 66.04 |
| 60.96 | 43.18 | 60.96 |
| 58.42 | 40.64 | 58.42 |
| 63.50 | 40.64 | 68.58 |
| 60.96 | 45.72 | 68.58 |
| 58.42 | 45.72 | 68.58 |

| ANOVA Source of Variation | Response Variable: | Spread (cm) of Mature Seed Stalk at Widest Point | | | |
|---|---|---|---|---|---|
| | df | SS | MS | F | P-value |
| Variety | 2 | 4046.66 | 2023.33 | 140.81 | <0.0001 |

| Variety | Mean | Tukey HSD Grouping |
|---|---|---|
| Pennylea | 62.74 | a |
| Buckskin | 61.72 | a |
| Quest | 44.83 | b |

ANOVA shows a significant difference (p < 0.05) in the spread (cm) of mature seed stalk at widest point, and the average mature seed stalk spread (cm) for Pennylea, Buckskin, and Quest is 62.74, 61.72, and 44.83, respectively. However, based on the Tukey HSD grouping, there are no differences between means for Pennylea and Buckskin.

TABLE 14

Height to width index of Mature Seed Stalk

| Buckskin | Quest | Pennylea |
|---|---|---|
| 2.44 | 3.06 | 1.56 |
| 2.50 | 3.17 | 1.73 |
| 2.70 | 3.29 | 1.65 |
| 2.83 | 3.44 | 1.64 |
| 3.00 | 3.50 | 1.95 |
| 2.68 | 3.11 | 1.65 |
| 2.23 | 3.00 | 1.91 |
| 2.26 | 2.79 | 1.64 |
| 2.44 | 3.06 | 1.67 |
| 2.44 | 2.60 | 1.90 |
| 2.54 | 3.24 | 1.90 |
| 2.44 | 3.06 | 1.84 |
| 2.61 | 3.06 | 1.88 |
| 2.48 | 2.84 | 1.80 |
| 2.52 | 2.94 | 1.62 |
| 2.54 | 3.06 | 1.71 |
| 2.65 | 3.50 | 1.74 |
| 2.48 | 3.44 | 1.56 |
| 2.58 | 3.00 | 1.56 |
| 2.65 | 2.94 | 1.59 |

| ANOVA Source of Variation | Response Variable: | Height to width index of Mature Seed Stalk | | | |
|---|---|---|---|---|---|
| | df | SS | MS | F | P-value |
| Variety | 2 | 19.29 | 9.64 | 271.27 | <0.0001 |

| Variety | Mean | Tukey HSD Grouping |
|---|---|---|
| Quest | 3.11 | a |
| Buckskin | 2.55 | b |
| Pennylea | 1.73 | c |

ANOVA shows a significant difference (p < 0.05) in the height to width index of mature seed stalk, and the average height to width index for Quest, Buckskin, and Pennylea is 3.11, 2.55, and 1.73, respectively.

Further Embodiments of the Invention

With the advent of molecular biological techniques that have allowed the isolation and characterization of genes that encode specific protein products, scientists in the field of plant biology developed a strong interest in engineering the genome of plants to contain and express foreign nucleic acids including additional or modified versions of native (endogenous) nucleic acids (optionally driven by a non-native promoter) in order to alter the traits of a plant in a specific manner. Any nucleic acid sequences, whether from a different species or from the same species, which are introduced into the genome using transformation or various breeding methods, are referred to herein collectively as "transgenes." Over the last fifteen to twenty years, several methods for producing transgenic plants have been developed, and in particular embodiments the present invention also relates to transformed versions of lettuce plants disclosed herein.

Genetic engineering techniques can be used (alone or in combination with breeding methods) to introduce one or more desired added traits into plant, for example, lettuce cultivar Buckskin or progeny or lettuce plants derived thereof.

Plant transformation generally involves the construction of an expression vector that will function in plant cells. Optionally, such a vector comprises one or more nucleic acids comprising a coding sequence for a polypeptide or an untranslated functional RNA under control of, or operatively linked to, a regulatory element (for example, a promoter). In representative embodiments, the vector(s) may be in the form of a plasmid, and can be used alone or in combination with other plasmids, to provide transformed lettuce plants using transformation methods as described herein to incorporate transgenes into the genetic material of the lettuce plant.

Additional methods include, but are not limited to, expression vectors introduced into plant tissues using a direct nucleic acid transfer method, such as microprojectile-mediated delivery (e.g., with a biolistic device), DNA injection, *Agrobacterium*-mediated transformation, electroporation, and the like. Transformed plants obtained from the plants (and parts and tissue culture thereof) of the invention are intended to be within the scope of this invention.

Expression Vectors for Plant Transformation—Selectable Markers.

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

One commonly used selectable marker for plant transformation is a neomycin phosphotransferase II (nptII) coding sequence, for example, isolated from transposon Tn5, which when placed under the control of plant regulatory signals confers resistance to kanamycin. Fraley, et al., PNAS, 80:4803 (1983). Another commonly used selectable marker is hygromycin phosphotransferase, which confers resistance to the antibiotic hygromycin. Vanden Elzen, et al., Plant Mol. Biol., 5:299 (1985).

Additional selectable markers of bacterial origin that confer resistance to antibiotics include gentamycin acetyl transferase, streptomycin phosphotransferase, aminoglycoside-3'-adenyl transferase, the bleomycin resistance determinant. Hayford, et al., Plant Physiol., 86:1216 (1988); Jones, et al., Mol. Gen. Genet., 210:86 (1987); Svab, et al., Plant Mol. Biol., 14:197 (1990); Hille, et al., Plant Mol. Biol., 7:171 (1986). Other selectable markers confer resistance to herbicides such as glyphosate, glufosinate, or bromoxynil. Comai, et al., Nature, 317:741-744 (1985); Gordon-Kamm, et al., Plant Cell, 2:603-618 (1990); and Stalker, et al., Science, 242:419-423 (1988).

Selectable markers for plant transformation that are not of bacterial origin include, for example, mouse dihydrofolate reductase, plant 5-enolpyruvylshikimate-3-phosphate synthase, and plant acetolactate synthase. Eichholtz, et al., Somatic Cell Mol. Genet., 13:67 (1987); Shah, et al., Science, 233:478 (1986); and Charest, et al., Plant Cell Rep., 8:643 (1990).

Another class of selectable marker for plant transformation involves screening of presumptively transformed plant cells rather than direct genetic selection of transformed cells for resistance to a toxic substance such as an antibiotic. These selectable markers are particularly useful to quantify or visualize the spatial pattern of expression of a transgene in specific tissues and are frequently referred to as a reporter gene because they can be fused to transgene or regulatory sequence for the investigation of nucleic acid expression. Commonly used reporters for screening presumptively transformed cells include alpha-glucuronidase (GUS), alpha-galactosidase, luciferase and chloramphenicol, acetyltransferase. Jefferson, R. A., Plant Mol. Biol., 5:387 (1987); Teeri, et al., EMBO J., 8:343 (1989); Koncz, et al., PNAS, 84:131 (1987); and DeBlock, et al., EMBO J., 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., J. Cell Biol., 115:151a (1991).

Green Fluorescent Protein (GFP) is also utilized as a marker for nucleic acid expression in prokaryotic and eukaryotic cells. Chalfie, et al., Science, 263:802 (1994). GFP and mutants of GFP may be used as screenable markers.

Expression Vectors for Plant Transformation—Promoters.

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter preferentially drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters:

An inducible promoter is operably linked to a nucleic acid for expression in a plant. Optionally, the inducible promoter is operably linked to a nucleotide sequence encoding a signal sequence which is operably linked to a nucleic acid for expression in the plant. With an inducible promoter, the rate of transcription increases in response to an inducing agent.

Any inducible promoter can be used in the instant invention. See Ward, et al., Plant Mol. Biol., 22:361-366 (1993). Exemplary inducible promoters include, but are not limited to, that from the ACEI system which responds to copper (Melt, et al., PNAS, 90:4567-4571 (1993)); promoter from the In2 gene from maize which responds to benzenesulfonamide herbicide safeners (Hershey, et al., Mol. Gen. Genet., 227:229-237 (1991) and Gatz, et al., Mol. Gen. Genet., 243:32-38 (1994)) or Tet repressor from Tn10 (Gatz, et al., Mol. Gen. Genet., 227:229-237 (1991)). A representative inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., PNAS, 88:0421 (1991).

B. Constitutive Promoters:

A constitutive promoter is operably linked to a nucleic acid for expression in a plant or the constitutive promoter is operably linked to a nucleotide sequence encoding a signal sequence which is operably linked to a nucleic acid for expression in a plant.

Many different constitutive promoters can be utilized in the instant invention. Exemplary constitutive promoters include, but are not limited to, the promoters from plant viruses such as the 35S promoter from CaMV (Odell, et al., Nature, 313:810-812 (1985)) and the promoters from such genes as rice actin (McElroy, et al., Plant Cell, 2:163-171 (1990)); ubiquitin (Christensen, et al., Plant Mol. Biol., 12:619-632 (1989) and Christensen, et al., Plant Mol. Biol., 18:675-689 (1992)); pEMU (Last, et al., Theor. Appl. Genet., 81:581-588 (1991)); MAS (Velten, et al., EMBO J., 3:2723-2730 (1984)) and maize H3 histone (Lepetit, et al., Mol. Gen. Genet., 231:276-285 (1992) and Atanassova, et al., Plant J., 2 (3): 291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT Application No. WO 96/30530.

C. Tissue-Specific or Tissue-Preferred Promoters:

A tissue-specific promoter is operably linked to a nucleic acid for expression in a plant. Optionally, the tissue-specific promoter is operably linked to a nucleotide sequence encoding a signal sequence which is operably linked to a nucleic acid for expression in a plant. Plants transformed with a nucleic acid of interest operably linked to a tissue-specific promoter transcribe the nucleic acid of interest exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., Science, 23:476-482 (1983) and Sengupta-Gopalan, et al., PNAS, 82:3320-3324 (1985)); a leaf-specific and light-induced promoter such as that from cab or rubisco (Simpson, et al., EMBO J., 4(11):2723-2729 (1985) and Timko, et al., Nature, 318:579-582 (1985)); an anther-specific promoter such as that from LAT52 (Twell, et al., Mol. Gen. Genet., 217:240-245 (1989)); a pollen-specific promoter such as that from Zm13 (Guerrero, et al., Mol. Gen. Genet., 244:161-168 (1993)) or a microspore-preferred promoter such as that from apg (Twell, et al., Sex. Plant Reprod., 6:217-224 (1993)).

Signal Sequences for Targeting Proteins to Subcellular Compartments.

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Polypeptide Transgenes and Agronomic Transgenes.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign polypeptide then can be extracted from a tissue of interest or from total biomass. Protein extraction from plant biomass can be accomplished by known methods which are discussed, for example, by Heney and Orr, Anal. Biochem., 114:92-6 (1981).

According to a representative embodiment, the transgenic plant provided for commercial production of foreign protein is a lettuce plant of the invention. In another embodiment, the biomass of interest is seed. For the relatively small number of transgenic plants that show higher levels of expression, a genetic map can be generated, for example via conventional RFLP, PCR, and SSR analysis, which identifies the approximate chromosomal location of the integrated DNA molecule. For exemplary methodologies in this regard, see Methods in Plant Molecular Biology and Biotechnology, Glick and Thompson Eds., 269:284, CRC Press, Boca Raton (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons can involve hybridizations, RFLP, PCR, SSR, and sequencing, all of which are conventional techniques.

Likewise, by means of the present invention, agronomic transgenes and other desired added traits can be expressed in transformed plants (and their progeny, e.g., produced by breeding methods). More particularly, plants can be genetically engineered to express various phenotypes of agronomic interest or other desired added traits. Exemplary nucleic acids of interest in this regard conferring a desired added trait(s) include, but are not limited to, those categorized below:

A. Transgenes that Confer Resistance to Pests or Disease:

1. Plant disease resistance transgenes. Plant defenses are often activated by specific interaction between the product of a disease resistance gene (R) in the plant and the product of a corresponding avirulence (Avr) gene in the pathogen. A plant line can be transformed with a cloned resistance transgene to engineer plants that are resistant to specific pathogen strains. See, for example, Jones, et al., Science, 266:789 (1994) (cloning of the tomato Cf-9 gene for resistance to *Cladosporium fulvum*); Martin, et al., Science, 262:1432 (1993) (tomato Pto gene for resistance to *Pseudomonas syringae* pv. tomato encodes a protein kinase); and Mindrinos, et al., Cell, 78:1089 (1994) (*Arabidopsis* RSP2 gene for resistance to *Pseudomonas syringae*).

2. A *Bacillus thuringiensis* protein, a derivative thereof, or a synthetic polypeptide modeled thereon. See, for example, Geiser, et al., Gene, 48:109 (1986), who disclose the cloning and nucleotide sequence of a Bt delta-endotoxin gene. Moreover, DNA molecules encoding delta-endotoxin transgenes can be purchased from American Type Culture Collection, Manassas, Va., for example, under ATCC Accession Nos. 40098, 67136, 31995, and 31998.

3. A lectin. See, for example, the disclosure by Van Damme, et al., Plant Mol. Biol., 24:25 (1994), who disclose the nucleotide sequences of several *Clivia miniata* mannose-binding lectin transgenes.

4. A vitamin-binding protein such as avidin. See, e.g., PCT Application No. US 93/06487. The application teaches the use of avidin and avidin homologues as larvicides against insect pests.

5. An enzyme inhibitor, for example, a protease or proteinase inhibitor, or an amylase inhibitor. See, for example, Abe, et al., J. Biol. Chem., 262: 16793 (1987) (nucleotide sequence of rice cysteine proteinase inhibitor); Huub, et al., Plant Mol. Biol., 21:985 (1993) (nucleotide sequence of cDNA encoding tobacco proteinase inhibitor I); and Sumitani, et al., Biosci. Biotech. Biochem., 57: 1243 (1993) (nucleotide sequence of *Streptomyces nitrosporeus* alpha-amylase inhibitor).

6. An insect-specific hormone or pheromone, such as an ecdysteroid and juvenile hormone, a variant thereof, a mimetic based thereon, or an antagonist or agonist thereof. See, for example, the disclosure by Hammock, et al., Nature, 344: 458 (1990), of baculovirus expression of cloned juvenile hormone esterase, an inactivator of juvenile hormone.

7. An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor) and Pratt, et al., Biochem. Biophys. Res. Comm., 163:1243 (1989) (an allostatin is identified in *Diploptera puntata*). See also, U.S. Pat. No. 5,266,317 to Tomalski, et al., who disclose transgenes encoding insect-specific, paralytic neurotoxins.

8. An insect-specific venom produced in nature, by a snake, a wasp, etc. For example, see Pang, et al, Gene, 116:165 (1992), for disclosure of heterologous expression in plants of a transgene coding for a scorpion insectotoxic peptide.

9. An enzyme responsible for a hyper-accumulation of a monoterpene, a sesquiterpene, a steroid, hydroxamic acid, a phenylpropanoid derivative, or another non-protein molecule with insecticidal activity.

10. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase transgene. DNA molecules which contain chitinase-encoding sequences can be obtained, for example, from the ATCC under Accession Nos. 39637 and 67152. See also, Kramer, et al., Insect Biochem. Mol. Biol., 23:691 (1993), who teach the nucleotide sequence of a cDNA encoding tobacco hornworm chitinase, and Kawalleck, et al., Plant Mol. Biol., 21:673 (1993), who provide the nucleotide sequence of the parsley ubi4-2 polyubiquitin transgene.

11. A molecule that stimulates signal transduction. For example, see the disclosure by Botella, et al., Plant Mol. Biol., 24:757 (1994), of nucleotide sequences for mung bean calmodulin cDNA clones, and Griess, et al., Plant Physiol., 104:1467 (1994), who provide the nucleotide sequence of a maize calmodulin cDNA clone.

12. A hydrophobic moment peptide. See PCT Application No. WO 95/16776 (disclosure of peptide derivatives of tachyplesin which inhibit fungal plant pathogens) and PCT Application No. WO 95/18855 (teaches synthetic antimicrobial peptides that confer disease resistance).

13. A membrane permease, a channel former, or a channel blocker. For example, see the disclosure of Jaynes, et al., Plant Sci., 89:43 (1993), of heterologous expression of a cecropin-beta, lytic peptide analog to render transgenic tobacco plants resistant to *Pseudomonas solanacearum*.

14. A viral-invasive protein or a complex toxin derived therefrom. For example, the accumulation of viral coat proteins in transformed plant cells imparts resistance to viral infection and/or disease development effected by the virus from which the coat protein transgene is derived, as well as by related viruses. See Beachy, et al., Ann. Rev. Phytopathol., 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

15. An insect-specific antibody or an immunotoxin derived therefrom. Thus, an antibody targeted to a critical metabolic function in the insect gut would inactivate an affected enzyme, killing the insect. See Taylor, et al., Abstract #497, Seventh Intl Symposium on Molecular Plant-Microbe Interactions, Edinburgh, Scotland (1994) (enzymatic inactivation in transgenic tobacco via production of single-chain antibody fragments).

16. A virus-specific antibody. See, for example, Tavladoraki, et al., Nature, 366:469 (1993), who show that transgenic plants expressing recombinant antibody transgenes are protected from virus attack.

17. A developmental-arrestive protein produced in nature by a pathogen or a parasite. Thus, fungal endo-alpha-1,4-D-polygalacturonases facilitate fungal colonization and plant nutrient released by solubilizing plant cell wall homo-alpha-1,4-D-galacturonase. See Lamb, et al., Bio/technology, 10:1436 (1992). The cloning and characterization of a transgene which encodes a bean endopolygalacturonase-inhibiting protein is described by Toubart, et al., Plant J., 2:367 (1992).

18. A developmental-arrestive protein produced in nature by a plant. For example, Logemann, et al., Bio/technology, 10:305 (1992), have shown that transgenic plants expressing the barley ribosome-inactivating transgene have an increased resistance to fungal disease.

19. A lettuce mosaic potyvirus (LMV) coat protein transgene introduced into *Lactuca sativa* in order to increase its resistance to LMV infection. See Dinant, et al., *Mol. Breeding*, 3:1, 75-86 (1997).

Any disease or present resistance transgenes, including those exemplified above, can be introduced into a lettuce plant of the invention through a variety of means including but not limited to transformation and breeding.

B. Transgenes that Confer Resistance to an Herbicide:

Exemplary polynucleotides encoding polypeptides that confer traits desirable for herbicide resistance include acetolactate synthase (ALS) mutants that lead to herbicide resistance such as the S4 and/or Hra mutations ((resistance to herbicides including sulfonylureas, imidazolinones, triazolopyrimidines, pyrimidinyl thiobenzoates); glyphosate resistance (e.g., 5-enol-pyrovyl-shikimate-3-phosphate-synthase (EPSPS) transgene, including but not limited to those described in U.S. Pat. Nos. 4,940,935, 5,188,642, 5,633,435, 6,566,587, 7,674,598 as well as all related application; or the glyphosate N-acetyltransferase (GAT) transgene, described in Castle et al., Science, 2004, 304:1151-1154; and in U.S. Patent Application Publication Nos. 20070004912, 20050246798, and 20050060767)); glufosinate resistance (e.g., BAR; see e.g., U.S. Pat. No. 5,561,236); 2,4-D resistance (e.g., aryloxy alkanoate dioxygenase or AAD-1, AAD-12, or AAD-13), HPPD resistance (e.g., *Pseudomonas* HPPD) and PPO resistance (e.g., fomesafen, acifluorfen-sodium, oxyfluorfen, lactofen, fluthiacet-methyl, saflufenacil, flumioxazin, flumiclorac-pentyl, carfentrazone-ethyl, sulfentrazone); a cytochrome P450 or variant thereof that confers herbicide resistance or tolerance to, inter alia, HPPD-inhibiting herbicides, PPO-inhibiting herbicides and ALS-inhibiting herbicides (U.S. Patent Application Publication No. 20090011936; U.S. Pat. Nos. 6,380,465; 6,121,512; 5,349,127; 6,649,814; and 6,300,544; and PCT International Publication No. WO 2007/000077); dicamba resistance (e.g., dicamba monoxygenase), and traits desirable for processing or process products such as high oil (e.g., U.S. Pat. No. 6,232,529); modified oils (e.g., fatty acid desaturase transgenes (U.S. Pat. No. 5,952,544; PCT International Publication No. WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al., J. Bacteriol., 1988, 170:5837-5847) facilitate expression of polyhydroxyalkanoates (PHAs)).

In embodiments, the polynucleotide encodes a polypeptide conferring resistance to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile.

Any transgene conferring herbicide resistance, including those exemplified above, can be introduced into the lettuce plants of the invention through a variety of means including, but not limited to, transformation (e.g., genetic engineering techniques) and crossing.

C. Transgenes that Confer or Contribute to a Value-Added Trait:

1. Increased iron content of the lettuce, for example, by introducing into a plant a soybean ferritin transgene as described in Goto, et al., *Acta Horticulturae.*, 521, 101-109 (2000).

2. Decreased nitrate content of leaves, for example, by introducing into a lettuce a transgene coding for a nitrate reductase. See, for example, Curtis, et al., Plant Cell Rep., 18: 11, 889-896 (1999).

3. Increased sweetness of the lettuce by introducing a transgene coding for monellin that elicits a flavor 100,000 times sweeter than sugar on a molar basis. See Penarrubia, et al., *Bio/technology,* 10: 561-564 (1992).

4. Modified fatty acid metabolism, for example, by introducing into a plant an antisense sequence directed against stearyl-ACP desaturase to increase stearic acid content of the plant. See Knultzon, et al., PNAS, 89: 2625 (1992).

5. Modified carbohydrate composition effected, for example, by introducing into plants a transgene coding for an enzyme that alters the branching pattern of starch. See Shiroza, et al., J. Bacteria, 170: 810 (1988) (nucleotide sequence of *Streptococcus* mutants fructosyltransferase transgene); Steinmetz, et al., Mol. Gen. Genet., 20: 220 (1985) (nucleotide sequence of *Bacillus subtilis* levansucrase transgene); Pen, et al., Bio/technology, 10: 292 (1992) (production of transgenic plants that express *Bacillus lichenifonnis* alpha-amylase); Elliot, et al., Plant Mol. Biol., 21: 515 (1993) (nucleotide sequences of tomato invertase transgenes); Sogaard, et al., J. Biol. Chem., 268: 22480 (1993) (site-directed mutagenesis of barley alpha-amylase transgene); and Fisher, et al., Plant Physiol., 102: 1045 (1993) (maize endosperm starch branching enzyme II).

Any transgene that confers or contributes a value-added trait, including those exemplified above, can be introduced into the lettuce plants of the invention through a variety of means including, but not limited to, transformation (e.g., genetic engineering techniques) and crossing.

D. Transgenes that Control Male-Sterility:

1. Introduction of a deacetylase transgene under the control of a tapetum-specific promoter and with the application of the chemical N-Ac-PPT. See, e.g., International Publication WO 01/29237.

2. Introduction of various stamen-specific promoters. See, e.g., International Publications WO 92/13956 and WO 92/13957.

3. Introduction of the barnase and the barstar transgenes. See, e.g., Paul, et al., Plant Mol. Biol., 19:611-622 (1992).

Any transgene that controls male sterility, including those exemplified above, can be introduced into the lettuce plants of the invention through a variety of means including, but not limited to, transformation (e.g., genetic engineering techniques) and crossing.

Methods for Plant Transformation.

Numerous methods for plant transformation have been developed, including biological and physical, plant transformation protocols. See, for example, Miki, et al., "Procedures for Introducing Foreign DNA into Plants" in Methods in Plant Molecular Biology and Biotechnology, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson Eds., CRC Press, Inc., Boca Raton, pp. 89-119 (1993).

A. *Agrobacterium*-Mediated Transformation.

One method for introducing an expression vector into plants is based on the natural transformation system of *Agrobacterium*. See, for example, Horsch, et al., Science, 227:1229 (1985); Curtis, et al., Journal of Experimental Botany, 45:279, 1441-1449 (1994); Torres, et al., Plant Cell Tissue and Organ Culture, 34:3, 279-285 (1993); and Dinant, et al., Molecular Breeding, 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci., 10:1 (1991). Descriptions of *Agrobacterium* vector systems and methods for *Agrobacterium*-mediated transgene transfer are provided by Gruber, et al., supra, Miki, et al., supra, and Moloney, et al., Plant Cell Rep., 8:238 (1989). See also, U.S. Pat. No. 5,591,616 issued Jan. 7, 1997.

B. Direct Transgene Transfer.

Several methods of plant transformation collectively referred to as direct transgene transfer have been developed as an alternative to *Agrobacterium*-mediated transformation. A generally applicable method of plant transformation is microprojectile-mediated transformation wherein DNA is carried on the surface of microprojectiles measuring 1 micron to 4 micron. The expression vector is introduced into plant tissues with a biolistic device that accelerates the microprojectiles to speeds of 300 m/s to 600 m/s which is sufficient to penetrate plant cell walls and membranes. Russell, D. R., et al., Plant Cell Rep., 12 (3, January), 165-169 (1993); Aragao, F. J. L., et al., Plant Mol. Biol., 20 (2, October), 357-359 (1992); Aragao, F. J. L., et al., Plant Cell Rep., 12 (9, July), 483-490 (1993); Aragao, Theor. Appl. Genet., 93:142-150 (1996); Kim, J., Minamikawa, T., Plant Sci., 117:131-138 (1996); Sanford, et al., Part. Sci. Technol., 5:27 (1987); Sanford, J. C., Trends Biotech., 6:299 (1988); Klein, et al., Bio/technology, 6:559-563 (1988); Sanford, J. C., Physiol. Plant, 7:206 (1990); Klein, et al., Bio/technology, 10:268 (1992).

Another method for physical delivery of DNA to plants is sonication of target cells. Zhang, et al., Bio/technology, 9:996 (1991). Alternatively, liposome and spheroplast fusion have been used to introduce expression vectors into plants. Deshayes, et al., EMBO J., 4:2731 (1985) and Christou, et al., PNAS, 84:3962 (1987). Direct uptake of DNA into protoplasts using CaCl.sub.2 precipitation, polyvinyl alcohol, or poly-L-ornithine has also been reported. Hain, et al., Mol. Gen. Genet., 199:161 (1985) and Draper, et al., Plant Cell Physiol., 23:451 (1982). Electroporation of protoplasts and whole cells and tissues have also been described. Saker, M., Kuhne, T., Biologia Plantarum, 40(4):507-514 (1997/98); Donn, et al., In Abstracts of VIIth International Congress on Plant Cell and Tissue Culture IAPTC, A2-38, p. 53 (1990); D'Halluin, et al., Plant Cell, 4:1495-1505 (1992); and Spencer, et al., Plant Mol. Biol., 24:51-61 (1994). See also Chupean, et al., Bio/technology, 7:5, 503-508 (1989).

Following transformation of plant target tissues, expression of the above-described selectable marker transgenes allows for preferential selection of transformed cells, tissues and/or plants, using regeneration and selection methods now well known in the art.

The foregoing methods for transformation would typically be used for producing a transgenic lettuce line. The transgenic lettuce line could then be crossed with another (non-transformed or transformed) line in order to produce a new transgenic lettuce line. Alternatively, a genetic trait that has been engineered into a particular plant cultivar using the foregoing transformation techniques could be introduced into another line using traditional breeding (e.g., backcrossing) techniques that are well known in the plant breeding arts. For example, a backcrossing approach could be used to move an engineered trait from a public, non-elite inbred line into an elite inbred line, or from an inbred line containing a foreign transgene in its genome into an inbred line or lines which do not contain that transgene. As used herein, "crossing" can refer to a simple X by Y cross, or the process of backcrossing, depending on the context.

Gene Conversions.

When the term "lettuce plant" is used in the context of the present invention, this term also includes any gene conversions of that plant or variety. The term "gene converted plant" as used herein refers to those lettuce plants that are developed, for example, by backcrossing, genetic engineering and/or mutation, wherein essentially all of the desired morphological and physiological characteristics of a variety are recovered in addition to the one or more genes transferred into the variety. To illustrate, backcrossing methods can be used with the present invention to improve or introduce a characteristic into the variety. The term "backcrossing" as used herein refers to the repeated crossing of a hybrid progeny back to the recurrent parent, e.g., backcrossing 1, 2, 3, 4, 5, 6, 7, 8, 9, or more times to the recurrent parent. The parental plant that contributes the gene for the desired characteristic is termed the "nonrecurrent" or "donor parent." This terminology refers to the fact that the nonrecurrent parent is generally used one time in the breeding e.g., backcross) protocol and therefore does not recur. The gene that is transferred can be a native gene, a mutated native gene or a transgene introduced by genetic engineering techniques into the plant (or ancestor thereof). The parental plant into which the gene(s) from the nonrecurrent parent are transferred is known as the "recurrent" parent as it is used for multiple rounds in the backcrossing protocol. Poehlman & Sleper (1994) and Fehr (1993). In a typical backcross protocol, the original variety of interest (recurrent parent) is crossed to a second variety (nonrecurrent parent) that carries the gene(s) of interest to be transferred. The resulting progeny from this cross are then crossed again to the recurrent parent and the process is repeated until a plant is obtained wherein essentially all of the desired morphological and physiological characteristics of the recurrent parent are recovered in the converted plant in addition to the transferred gene(s) and associated trait(s) from the nonrecurrent parent.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, pest or disease resistance (e.g., resistance to bacterial, fungal, or viral disease), insect resistance, enhanced nutritional quality, increased sweetness, increased flavor, improved ripening control, improved salt tolerance, industrial usage, yield stability, and yield enhancement. These genes are generally inherited through the nucleus.

Tissue Culture.

Further reproduction of lettuce plants variety can occur by tissue culture and regeneration. Tissue culture of various tissues of lettuce and regeneration of plants therefrom is well known and widely published. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28(2), 139-145 (1992). It is clear from the literature that the state of the art is such that these methods of obtaining plants are routinely used and have a very high rate of success. Thus, another aspect of this invention is to provide cells which upon growth and differentiation produce lettuce plants having desired characteristics of lettuce cultivar Buckskin. Optionally, lettuce plants can be regenerated from the tissue culture of the invention comprising all or essentially all of the physiological and morphological characteristics of lettuce cultivar Buckskin.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques.

Additional Breeding Methods.

This invention is also directed to methods for producing a lettuce plant by crossing a first parent lettuce plant with a second parent lettuce plant wherein the first or second parent lettuce plant is a plant of lettuce cultivar Buckskin. Further, both first and second parent lettuce can come from lettuce cultivar Buckskin. Thus, any of the following exemplary methods using lettuce cultivar Buckskin are part of this invention: selfing, backcrosses, hybrid production, crosses to populations, double haploid production, and the like. All plants produced using lettuce cultivar Buckskin as at least one parent are within the scope of this invention, including those developed from lettuce plants derived from lettuce cultivar Buckskin. Advantageously, lettuce cultivar Buckskin can be used in crosses with other, different, lettuce plants to produce the first generation ($F_1$) lettuce hybrid seeds and plants with desirable characteristics. The lettuce plants of the invention can also be used for transformation where exogenous transgenes are introduced and expressed by the plants of the invention. Genetic variants created either through traditional breeding methods or through transformation of the cultivars of the invention by any of a number of protocols known to those of skill in the art are intended to be within the scope of this invention.

The following describes exemplary breeding methods that may be used with lettuce cultivar Buckskin in the development of further lettuce plants. One such embodiment is a method for developing lettuce cultivar Buckskin progeny lettuce plants in a lettuce plant breeding program comprising: obtaining a plant, or a part thereof, of lettuce cultivar Buckskin, utilizing said plant or plant part as a source of breeding material, and selecting a lettuce cultivar Buckskin progeny plant with molecular markers in common with lettuce cultivar Buckskin and/or with some, all or essentially all of the morphological and/or physiological characteristics of lettuce cultivar Buckskin (see, e.g., Tables 1 to 14). In representative embodiments, the progeny plant has at least 1, 2, 3, 4, 5, 6, 7, 8, 9, 10 or more of the morphological and physiological characteristics of lettuce cultivar Buckskin (e.g., as described in Tables 1 to 14) and intermediate resistance to LMV strain Ls-1, or even all of the morphological and physiological characteristics of lettuce cultivar Buckskin so that said progeny lettuce plant is not significantly different for said traits than lettuce cultivar Buckskin, as determined at the 5% significance level when grown in the same environmental conditions; optionally, with the presence of one or more desired additional traits (e.g., male sterility, disease resistance, pest or insect resistance, herbicide resistance, and the like). Breeding steps that may be used in the breeding program include pedigree breeding, backcrossing, mutation breeding and/or recurrent selection. In conjunction with these steps, techniques such as RFLP-enhanced selection, genetic marker enhanced selection (for example, SSR markers) and/or and the making of double haploids may be utilized.

Another representative method involves producing a population of lettuce cultivar Buckskin progeny plants, comprising crossing lettuce cultivar Buckskin with another lettuce plant, thereby producing a population of lettuce plants that, on average, derives at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from lettuce cultivar Buckskin, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of lettuce cultivar Buckskin. One embodiment of this invention is the lettuce plant produced by this method and that has obtained at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles from lettuce cultivar Buckskin, and optionally is the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology. A plant of this population may be selected and repeatedly selfed or sibbed with a lettuce plant resulting from these successive filial generations. Another approach is to make double haploid plants to achieve homozygosity.

One of ordinary skill in the art of plant breeding would know how to evaluate the traits of two plant varieties to determine if there is no significant difference between the two traits expressed by those varieties. For example, see Fehr and Walt, Principles of Cultivar Development, pp. 261-286 (1987). In embodiments, the invention encompasses Buckskin progeny plants having a combination of at least 2, 3, 4, 5, 6, 7, 8, 9, 10 or more of the characteristics as described herein for lettuce cultivar Buckskin, so that said progeny lettuce plant is not significantly different for said traits than lettuce cultivar Buckskin, as determined at the 5% significance level when grown in the same environmental conditions. Using techniques described herein and those known in the art, molecular markers may be used to identify said progeny plant as progeny of lettuce cultivar Buckskin. Mean trait values may be used to determine whether trait differences are significant, and optionally the traits are measured on plants grown under the same environmental conditions.

Progeny of lettuce cultivar Buckskin may also be characterized through their filial relationship with lettuce cultivar Buckskin, as for example, being within a certain number of breeding crosses of lettuce cultivar Buckskin. A breeding cross is a cross made to introduce new genetics into the progeny, and is distinguished from a cross, such as a self or a sib cross or a backcross to Buckskin as a recurrent parent, made to select among existing genetic alleles. The lower the number of breeding crosses in the pedigree, the closer the relationship between lettuce cultivar Buckskin and its progeny. For example, progeny produced by the methods described herein may be within 1, 2, 3, 4, 5 or more breeding crosses of lettuce cultivar Buckskin.

In representative embodiments, a lettuce plant derived from lettuce cultivar Buckskin comprises cells comprising at least one set of chromosomes derived from lettuce cultivar Buckskin. In embodiments, the lettuce plant or population of lettuce plants derived from lettuce cultivar Buckskin comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from lettuce cultivar Buckskin, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of lettuce cultivar Buckskin, and optionally is the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology. In embodiments, the lettuce plant derived from lettuce cultivar Buckskin is one, two, three, four, five or more breeding crosses removed from lettuce cultivar Buckskin.

In representative embodiments, a plant derived from lettuce cultivar Buckskin is a double haploid plant, a hybrid plant or an inbred plant.

In embodiments, a hybrid or derived plant from lettuce cultivar Buckskin comprises a desired added trait. In representative embodiments, a lettuce plant derived from lettuce cultivar Buckskin comprises all of the morphological and physiological characteristics of lettuce cultivar Buckskin (e.g., as described in Tables 1 to 14). In embodiments, the lettuce plant derived from lettuce cultivar Buckskin comprises essentially all of the morphological and physiological characteristics of lettuce cultivar Buckskin (e.g., as described in Tables 1 to 14) in any combination, with the addition of a desired added trait.

Those skilled in the art will appreciate that any of the traits described above with respect to plant transformation methods can be introduced into a plant of the invention (e.g., lettuce cultivar Buckskin and hybrid lettuce plants and other lettuce plants derived therefrom) using breeding techniques.

Genetic Analysis of Lettuce Cultivar Buckskin.

The invention further provides a method of determining a genetic characteristic of lettuce cultivar Buckskin or a progeny thereof, e.g., a method of determining a genotype of lettuce cultivar Buckskin or a progeny thereof. In embodiments, the method comprises detecting in the genome of a Buckskin plant, or a progeny plant thereof, at least a first polymorphism (e.g., using nucleic acid amplification, nucleic acid sequencing and/or one or more molecular markers). To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

DEPOSIT INFORMATION

Applicants have made a deposit of at least 625 seeds of lettuce cultivar Buckskin with the American Type Culture Collection (ATCC), 10801 University Boulevard, Manassas, Va., 20110-2209 U.S.A. under ATCC Deposit No. PTA-127130 on Sep. 15, 2021. This deposit of lettuce variety Buckskin will be maintained in the ATCC depository, which is a public depository, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§ 1.801-1.809, including providing an indication of the viability of the samples. Access to this deposit will be made available during the pendency of this application to the Commissioner upon request. Upon the issuance of a patent on the variety, the variety will be irrevocably and without restriction released to the public by providing access to the deposit of at least 2500 seeds of the variety with the ATCC. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC § 2321 et seq.).

The foregoing invention has been described in detail by way of illustration and example for purposes of clarity and understanding. However, it will be apparent that certain changes and modifications such as single gene modifications and mutations, somaclonal variants, variant individuals selected from large populations of the plants of the instant inbred and the like may be practiced within the scope of the invention.

What is claimed is:

1. A seed of lettuce cultivar Buckskin, a representative sample of seed having been deposited under ATCC Accession No. PTA-127130.

2. A plant of lettuce cultivar Buckskin, a representative sample of seed having been deposited under ATCC Accession No. PTA-127130.

3. A lettuce plant, or a part thereof, having of the physiological and morphological characteristics of the lettuce plant of claim 2.

4. An F1 progeny lettuce plant of the plant of claim 2.

5. A seed that produces the plant of claim 4.

6. A plant part of the lettuce plant of claim 2.

7. The plant part of claim 6, wherein the plant part is a leaf, pollen, an ovule, an anther, a root, or a cell.

8. A tissue culture of regenerable cells of the plant of claim 2.

9. A lettuce plant regenerated from the tissue culture of claim 8 or a selfed progeny thereof, wherein said lettuce plant expresses all of the physiological and morphological characteristics of lettuce cultivar Buckskin.

10. A processed product from the plant of claim 2, wherein the processed product comprises cut, sliced, ground, pureed, dried, canned, jarred, washed, packaged, frozen and/or heated leaves.

11. A method of producing lettuce seed, the method comprising crossing the plant of claim 2 with itself or a second lettuce plant and harvesting the resulting seed.

12. An F1 lettuce seed from a plant produced by the method of claim 11.

13. An F1 lettuce plant, or a meristem, leaf, pollen, cotyledon, hypocotyl, root, root tip, anther, flower, flower bud, pistil, ovule, shoot, stem, stalk, petiole, pith, capsule, scion, rootstock, or fruit pact thereof, produced by growing the seed of claim 12.

14. A doubled haploid plant produced from the F1 lettuce plant of claim 13.

15. A method for producing a seed of a lettuce plant derived from the plant of claim 2, the method comprising:
 (a) crossing a plant of lettuce cultivar Buckskin with a second lettuce plant; and
 (b) allowing seed to form;
 (c) growing a plant from the seed of step (b) to produce a plant derived from lettuce cultivar Buckskin;
 (d) selfing the plant of step (c) or crossing it to a second lettuce plant to form additional lettuce seed derived from lettuce cultivar Buckskin; and
 (e) optionally repeating steps (c) and (d) one or more times to generate further derived lettuce seed from lettuce cultivar Buckskin, wherein in step (c) a plant is grown from the additional lettuce seed of step (d) in place of growing a plant from the seed of step (b).

16. A seed produced by the method of claim 15, wherein the seed comprises at least 50% of the alleles of lettuce cultivar Buckskin and is within one breeding cross of lettuce cultivar Buckskin.

17. A plant, or part thereof, produced by growing the seed of claim 16.

18. A method of vegetatively propagating the plant of claim 2, the method comprising:
 (a) collecting tissue capable of being propagated from a plant of lettuce cultivar Buckskin;
 (b) cultivating the tissue to obtain proliferated shoots;
 (c) rooting the proliferated shoots to obtain rooted plantlets; and
 (d) optionally, growing plants from the rooted plantlets.

19. A lettuce plantlet or plant obtained by the method of claim 18, wherein the lettuce plantlet or plant expresses all of the physiological and morphological characteristics of lettuce cultivar Buckskin.

20. A method of introducing a desired added trait into lettuce cultivar Buckskin, the method comprising:
 (a) crossing the plant of claim 2 with a lettuce plant that comprises a desired added trait to produce F1 progeny;
 (b) selecting an F1 progeny that comprises the desired added trait;
 (c) crossing the selected F1 progeny with lettuce cultivar Buckskin to produce backcross progeny;
 (d) selecting a backcross progeny comprising the desired added trait; and
 (e) optionally repeating steps (c) and (d) one or more times to produce a further backcross progeny plant derived from lettuce cultivar Buckskin comprising a desired added trait and otherwise all of the physiological and morphological characteristics of lettuce cultivar Buckskin, wherein in step (c) the selected backcross progeny produced in step (d) is used in place of the selected F1 progeny of step (b).

21. The method of claim 20, wherein the desired added trait is male sterility, pest resistance, insect resistance, disease resistance, herbicide resistance, or any combination thereof.

22. A lettuce plant produced by the method of claim 20 or a selfed progeny thereof, wherein the lettuce plant is the backcross progeny of step (e) or a selfed progeny thereof and has the desired added trait and otherwise all of the physiological and morphological characteristics of lettuce cultivar Buckskin.

23. A seed that produces the plant of claim 22.

24. A method of producing a plant of lettuce cultivar Buckskin comprising a desired added trait, the method comprising introducing a transgene conferring the desired trait into the plant of claim 2.

25. A lettuce plant produced by the method of claim 24 or a selfed progeny thereof, wherein the lettuce plant is a transformed plant of lettuce cultivar Buckskin and has the desired added trait.

26. A seed of the plant of claim 25, wherein the seed produces a transformed plant of lettuce cultivar Buckskin that comprises the transgene and has the desired added trait.

27. A method of determining a genotype of lettuce cultivar Buckskin, the method comprising:
(a) obtaining a sample of nucleic acids from the plant of claim 2; and
(b) detecting a polymorphism in the nucleic acid sample.

28. A method of producing a lettuce leaf, the method comprising:
(a) growing the lettuce plant according to claim 2 to produce a lettuce leaf; and
(b) harvesting the lettuce leaf.

29. A method of producing a lettuce leaf, the method comprising:
(a) growing the lettuce plant according to claim 22 to produce a lettuce leaf; and
(b) harvesting the lettuce leaf.

* * * * *